(12) United States Patent
Bachmann et al.

(10) Patent No.: US 7,811,299 B2
(45) Date of Patent: Oct. 12, 2010

(54) CLOSURE SYSTEM FOR TUBULAR ORGANS

(75) Inventors: Michel Bachmann, Vaux sur Morges (CH); Christian Imbert, Froideville (CH); Alain Jordan, Lausanne (CH)

(73) Assignee: Allergan, Inc., Irvine, CA (US)

( * ) Notice: Subject to any disclaimer, the term of this patent is extended or adjusted under 35 U.S.C. 154(b) by 51 days.

(21) Appl. No.: 10/591,869

(22) PCT Filed: Mar. 5, 2005

(86) PCT No.: PCT/IB2005/050822

§ 371 (c)(1),
(2), (4) Date: Jun. 27, 2007

(87) PCT Pub. No.: WO2005/087147

PCT Pub. Date: Sep. 22, 2005

(65) Prior Publication Data

US 2007/0250085 A1   Oct. 25, 2007

(30) Foreign Application Priority Data

Mar. 8, 2004  (WO) .............. PCT/CH2004/000136

(51) Int. Cl.
*A61B 17/08* (2006.01)
(52) U.S. Cl. .................................... 606/157
(58) Field of Classification Search ............... 606/157, 606/201–203; 600/37; 24/16 PB, 30.5 P, 24/17 AP, 265 AL, 598.2, 20 R, 20 TT, 20 CW, 24/20 W, 275, 281
See application file for complete search history.

(56) References Cited

U.S. PATENT DOCUMENTS 1,830,947 A * 11/1931 Klingel ....................... 439/799
1,999,683 A *  4/1935 Borresen ..................... 24/275
2,339,138 A *  1/1944 Black ......................... 24/275
2,405,667 A *  8/1946 Ottesen ..................... 220/277
2,438,231 A *  3/1948 Schultz et al. .............. 401/244
2,635,907 A *  4/1953 Heimbuch .................. 277/553
2,714,469 A *  8/1955 Carlson ..................... 220/320
2,936,980 A *  5/1960 Rapata ..................... 24/16 PB
3,059,645 A * 10/1962 Hasbrouck et al. .......... 604/179
3,189,961 A *  6/1965 Heller ....................... 24/20 TT (Continued)

FOREIGN PATENT DOCUMENTS

EP       1 036 545 A2    9/2000

(Continued)

*Primary Examiner*—(Jackie) Tan-Uyen T Ho
*Assistant Examiner*—Son Dang
(74) *Attorney, Agent, or Firm*—Stephen Donovan; Allergan, Inc.

(57) ABSTRACT

In one embodiment, a surgically implantable adjustable ring comprises a ring body, which includes a closure system having first and second end parts. The ring body is designed to be closed around a tubular organ by the closure system, constricting the tubular organ by forming a loop. The first end part is shaped like a sleeve having a first and second end portions, and is designed to receive the second end part of the ring. The sleeve is substantially perpendicular to the main direction of the first end part of the ring, and the second end part of the ring includes a locking protrusion adapted to hold the sleeve in position, securing the ring in a closed position by engaging the locking protrusion in an opening disposed on the sleeve.

10 Claims, 2 Drawing Sheets

U.S. PATENT DOCUMENTS

| | | | |
|---|---|---|---|
| 4,176,412 A * | 12/1979 | Peterson | 4/144.1 |
| 4,271,827 A * | 6/1981 | Angelchik | 600/37 |
| 4,299,012 A * | 11/1981 | Oetiker | 24/19 |
| 4,442,153 A * | 4/1984 | Meltsch | 428/99 |
| 4,492,004 A * | 1/1985 | Oetiker | 24/20 R |
| 5,246,456 A * | 9/1993 | Wilkinson | 623/23.65 |
| 5,658,298 A * | 8/1997 | Vincent et al. | 606/139 |
| 6,511,490 B2 * | 1/2003 | Robert | 606/151 |
| 6,601,604 B1 | 8/2003 | Cooper | |
| 6,632,239 B2 * | 10/2003 | Snyder et al. | 606/213 |
| 6,676,674 B1 * | 1/2004 | Dudai | 606/151 |
| 7,060,080 B2 * | 6/2006 | Bachmann | 606/151 |
| 7,172,607 B2 * | 2/2007 | Hofle et al. | 606/151 |
| 7,240,607 B2 * | 7/2007 | Fish | 92/169.1 |
| 2003/0120288 A1 * | 6/2003 | Benchetrit | 606/151 |
| 2003/0158564 A1 * | 8/2003 | Benchetrit | 606/151 |
| 2004/0049209 A1 * | 3/2004 | Benchetrit | 606/151 |
| 2004/0068847 A1 * | 4/2004 | Belisle et al. | 24/279 |
| 2004/0153106 A1 * | 8/2004 | Dudai | 606/157 |
| 2005/0119672 A1 * | 6/2005 | Benchetrit | 606/151 |
| 2005/0143765 A1 * | 6/2005 | Bachmann et al. | 606/157 |
| 2005/0154274 A1 * | 7/2005 | Jarsaillon et al. | 600/407 |
| 2005/0251181 A1 * | 11/2005 | Bachmann | 606/157 |
| 2006/0212051 A1 * | 9/2006 | Snyder et al. | 606/151 |
| 2006/0252983 A1 * | 11/2006 | Lembo et al. | 600/37 |
| 2007/0015956 A1 * | 1/2007 | Crawford et al. | 600/37 |
| 2007/0044655 A1 * | 3/2007 | Fish | 92/169.1 |
| 2007/0213836 A1 * | 9/2007 | Paganon | 623/23.64 |

FOREIGN PATENT DOCUMENTS

| | | |
|---|---|---|
| EP | 1 036 545 A3 | 9/2000 |
| FR | 2823663 | 10/2002 |
| WO | WO01/085071 | 11/2001 |
| WO | WO 02/096326 A2 | 12/2002 |
| WO | WO03/059215 | 7/2003 |
| WO | WO 2004/108025 A1 | 12/2004 |

* cited by examiner

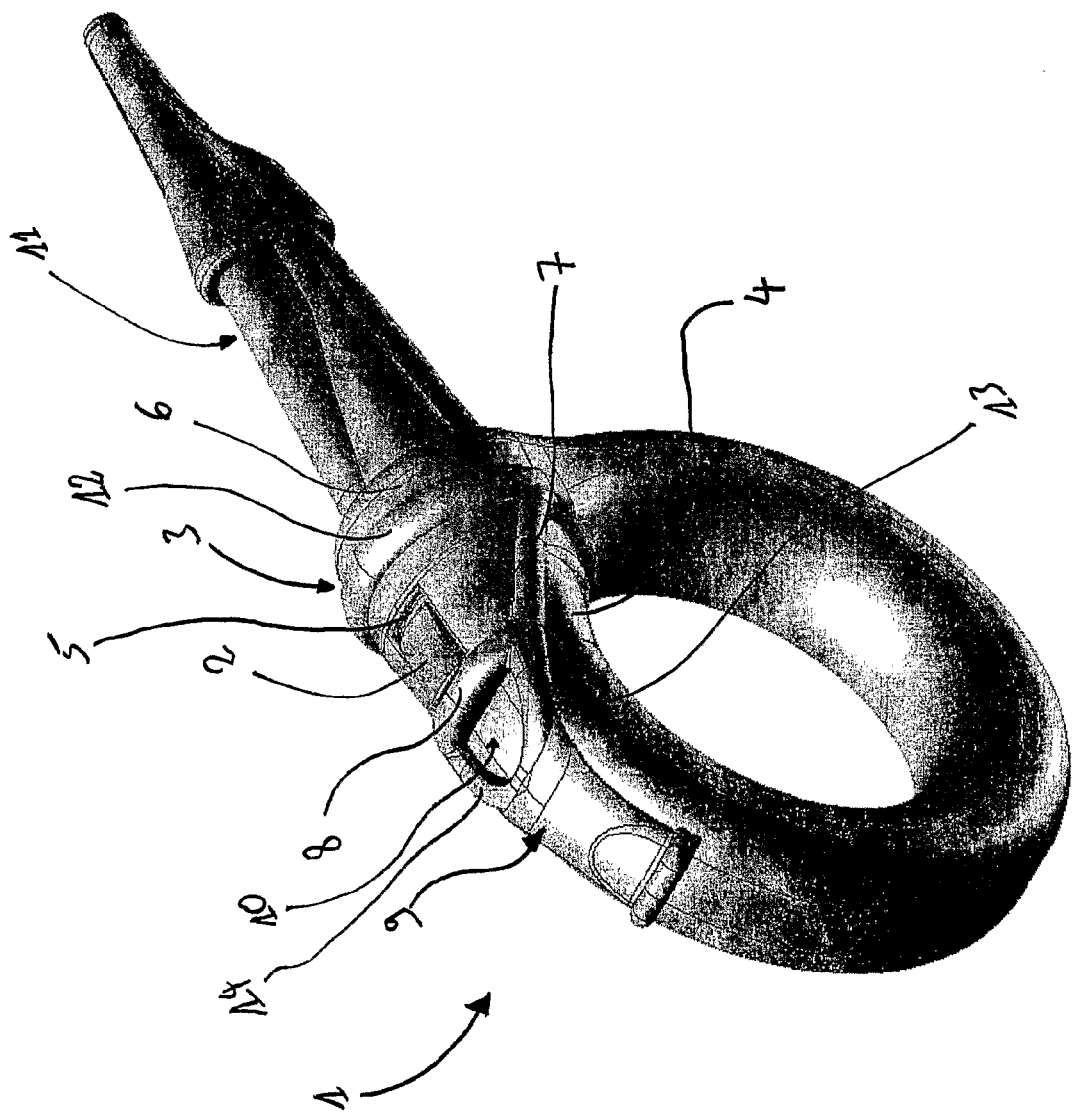

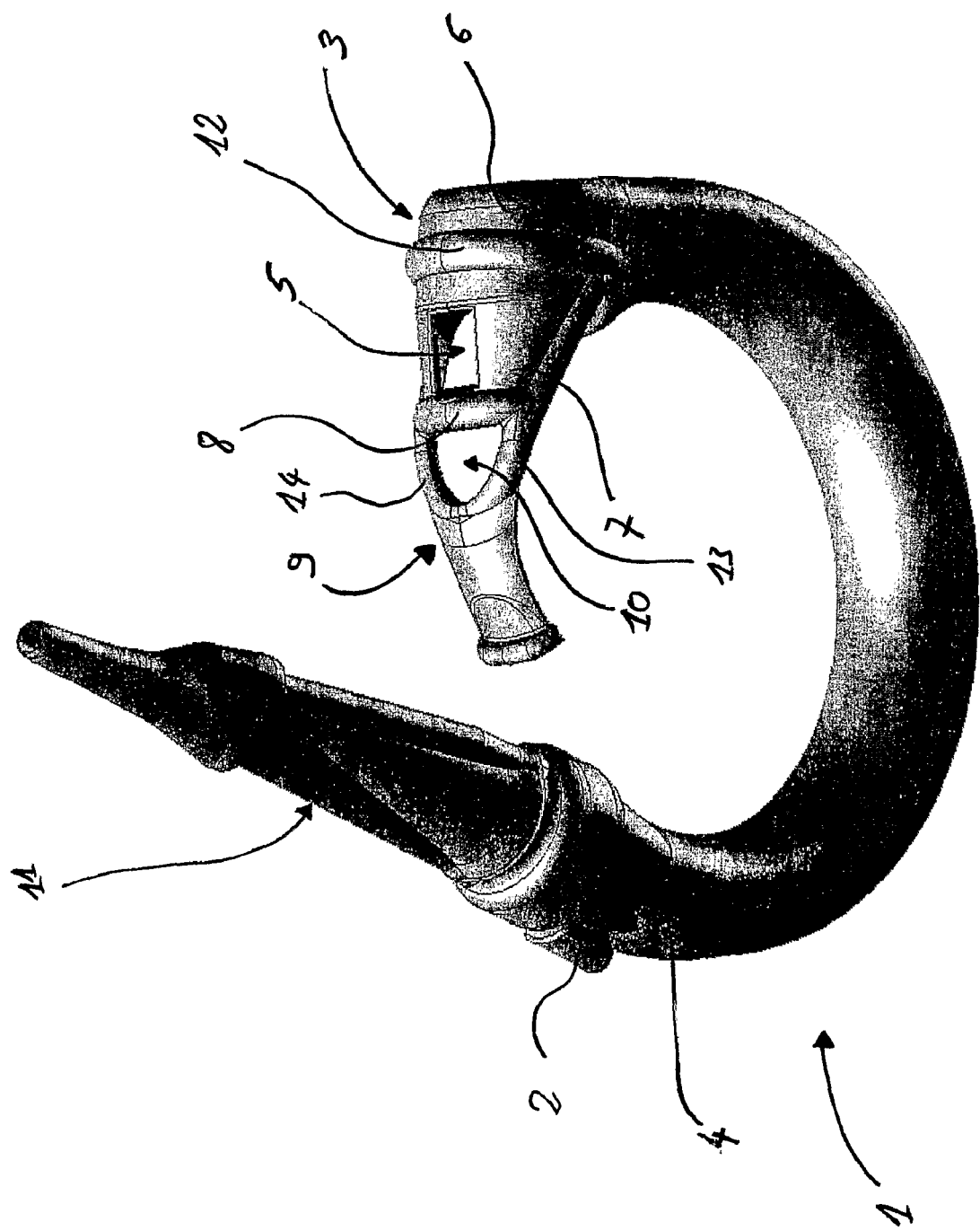

CLOSURE SYSTEM FOR TUBULAR ORGANS

FIELD OF THE INVENTION

The present invention relates to surgical devices for adjusting the diameter of tubular organs such as the esophagus, the stomach, the colon or the urethra. Such devices may be used as sphincters (e.g. as anal or urinary sphincters) or for the control of obesity. More particularly, the present invention relates to surgically implantable adjustable rings for encircling said tubular organs.

BACKGROUND OF THE INVENTION

Surgical devices for adjusting the diameter of tubular organs have been disclosed in the prior art, for example, in patent documents U.S. Pat. No. 5,658,298, U.S. Pat. No. 6,601,604, FR 2 823 663, WO 01/85071 and WO 03/059215.

In particular, the device disclosed in International Publication No. WO 03/059215 has an open ring shape that comprises a first and second end parts and that is designed to be closed around a tubular organ at the two end parts. A closure system adjusts the diameter of the tubular organ by forming the ring into a loop. The first end part of the ring is shaped like a sleeve and is designed to receive the second end part of the ring, the main axis of the sleeve being defined along a direction that is substantially perpendicular to the main direction of the first end part. The second part of the ring comprises instead a hook-shaped extension that is adapted to capture the edge of the second end part of the sleeve, and thereby to secure the ring in a closed position.

SUMMARY OF THE INVENTION

An object of the present invention is to provide a closure system improved over the devices in the prior art.

This and other objects of the present invention are achieved by providing a surgically implantable ring that can be adjusted in diameter. In one embodiment, a surgically adjustable ring constructed according to the principles of the present invention comprises an open ring body that is designed to constrict a tubular organ and that includes a closure system having a first and a second end parts. The first end part includes a sleeve that has a first and a second portion and that is designed to receive the second end part of the closure system. A locking protrusion extends from the second end part and is adapted to engage an aperture in the sleeve, thereby securing the ring in a closed position.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which:

FIG. 1 is a perspective view of an embodiment of the invention in a closed position; and FIG. 2 is a perspective view of the embodiment of FIG. 1 in an open position.

DETAILED DESCRIPTION OF THE INVENTION

An embodiment of the invention will be discussed in greater detail hereinafter.

Referring to FIGS. 1 and 2, adjustable ring 1 comprises a closure system having a first end part 3 and a second end part 4.

Ring 1 may be manufactured from any suitable material, for example, from a biocompatible elastomeric material. The external part of ring 1 may be more rigid than the internal part, which has an internal diameter that is adjustable.

First end part 3 is shaped like a sleeve designed to receive second end part 4, while second end part 4 has an extension 11 containing adjusting means, for instance, a wire which can be pulled or pushed in order to adjust the diameter of ring 1.

The sleeve on first end part 3 includes first end portion 6, which is reinforced by a flange 12, and second end portion 7, which contains aperture 5 designed to receive and efficiently retain protrusion 2, and which is engages second end part 4.

For the purpose of closing or opening ring 1, second end portion 7 of the sleeve is provided with an extension defining flexible tab 9, which contains opening 10 situated close to aperture 5. The presence of opening 10 in tab 9 provides several advantages, in particular the accidental opening of the closure system is prevented in situations where tab 9 has to support forces, tending to bend tab 9 in the direction of extension 11. Such forces may be due to the movement of the patient, or of the organs of the patient, or to the fluid or bolus passing through the tubular organ.

The area between aperture 5 and opening 10 is reinforced by flange 8. The other sides of opening 10 are also reinforced by flanges 13, 14.

The shape of protrusion 2 is designed to closely match the shape of flange 8.

The invention is of course not limited to the above described embodiment. In another embodiment, opening 10 may be replaced by a portion that is more flexible than the remaining part of tab 9. Such a more flexible portion may be obtained with different techniques, for example, by making that portion thinner than the rest of tab 9. In still another embodiment, the second portion of the sleeve may partially overlap the second part of the closure system when the ring in in closed position.

The invention may be advantageously used in a variety of applications, for instance, as a sphincter or as a gastric ring.

The invention claimed is:

1. A surgically implantable adjustable gastric ring for constricting a tubular organ, the adjustable gastric ring comprising:

an open ring body having closure system including a first and a second end parts, the open ring body being designed to be closed around the tubular organ;

the closure system constricting the tubular organ by closing the ring and forming the ring into a loop; and the first end part including a first reinforcement flange and a sleeve having a first and a second portions, the sleeve being designed to receive the second end part and having a tab extending from the second portion, the sleeve being disposed in a substantially perpendicular direction in relation to the direction of the first end part, the second part comprising a locking protrusion adapted to engage a first aperture in the sleeve, thereby securing the ring in a closed position;

wherein the tab defines a second aperture disposed substantially parallel to the first aperture and includes a second reinforcement flange located adjacent to and in between the first aperture and the second aperture comprises a portion more flexible than the remaining portion of the tab, the flexible portion being situated in the proximity of the aperture, the flexible portion preventing an accidental opening of the closure system after the adjustable gastric ring is disposed around the tubular organ.

2. The adjustable ring according to claim 1 wherein the first reinforcement flange is disposed transversally to the external perimeter of the ring.

3. The adjustable ring according to claim 1 wherein the ring is made of a biocompatible elastomeric material.

4. A closure system comprising: A surgically implantable adjustable gastric ring for constricting a tubular organ, the adjustable gastric ring comprising
   an open ring body;
   a first end part including:
      a sleeve having a first portion;
      a second portion defining an aperture;
      a third portion defining a tab hole adapted to prevent an accidental opening of the closure system after the adjustable gastric ring is disposed around the tubular organ and including a tab, the second portion positioned between the first and third portions;
      a first reinforcement flange positioned at the first portion;
      a second reinforcement flange disposed adjacent to and in between the aperture and the tab hole; and
   a second end part comprising a locking element protruding therefrom, the first and second end parts positioned at opposite ends of the ring body;
   wherein the tab hole remains substantially unfilled when the closure system is in a closed position.

5. The closure system according to claim 4 wherein the second end part and at least one of the portions of the first end part are substantially perpendicular to one another.

6. The closure system according to claim 4 wherein the tab hole has adjacent sides and a side reinforcement flange is positioned at each of the adjacent sides.

7. The closure system according to claim 4 further comprising adjusting means to adjust the ring body diameter.

8. The closure system according to claim 7 wherein the adjusting means is a wire.

9. The closure system of claim 4 wherein the tab is made of a flexible material.

10. The closure system of claim 9 wherein the tab comprises a portion more flexible than the remaining portion of the tab, the flexible portion being situated in the proximity of the aperture.

* * * * *

UNITED STATES PATENT AND TRADEMARK OFFICE
CERTIFICATE OF CORRECTION

| | | |
|---|---|---|
| PATENT NO. | : 7,811,299 B2 | Page 1 of 1 |
| APPLICATION NO. | : 10/591869 | |
| DATED | : October 12, 2010 | |
| INVENTOR(S) | : Michel Bachmann et al. | |

It is certified that error appears in the above-identified patent and that said Letters Patent is hereby corrected as shown below:

In column 2, lines 38-39, delete "in in" and insert -- is in --, therefor.

In column 3, line 8, in claim 4, delete "A surgically" and insert -- a surgically --, therefor.

Signed and Sealed this
Tenth Day of May, 2011

David J. Kappos
*Director of the United States Patent and Trademark Office*